US012733944B2

(12) United States Patent
Risley

(10) Patent No.: US 12,733,944 B2
(45) Date of Patent: Sep. 15, 2026

(54) METHODS FOR ANKLE SYNDESMOSIS REPAIR

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventor: Christina M. Risley, West Barnstable, MA (US)

(73) Assignees: Smith & Nephew, Inc., Memphis, TN (US); Smith & Nephew Orthopaedics AG, Zug (CH); Smith & Nephew Asia Pacific Pte. Limited, Singapore (SG)

(*) Notice: Subject to any disclaimer, the term of this patent is extended or adjusted under 35 U.S.C. 154(b) by 29 days.

(21) Appl. No.: 18/945,879

(22) Filed: Nov. 13, 2024

(65) Prior Publication Data

US 2025/0169832 A1 May 29, 2025

Related U.S. Application Data

(60) Provisional application No. 63/602,790, filed on Nov. 27, 2023.

(51) Int. Cl.
*A61B 17/17* (2006.01)
*A61B 17/04* (2006.01)

(52) U.S. Cl.
CPC ...... *A61B 17/1775* (2016.11); *A61B 17/0401* (2013.01)

(58) Field of Classification Search
CPC . A61B 17/04; A61B 17/1775; A61B 17/0401; A61B 17/0404; A61B 17/1682
USPC .................... 606/232–233, 228, 151, 96, 80; 623/21.18
See application file for complete search history.

(56) References Cited

U.S. PATENT DOCUMENTS

| | | | | |
|---|---|---|---|---|
| 5,306,290 A * | 4/1994 | Martins | A61B 17/0401 606/232 |
| 5,575,801 A * | 11/1996 | Habermeyer | A61B 17/1714 606/232 |
| 5,766,221 A * | 6/1998 | Benderev | A61B 17/0644 606/232 |
| 10,779,868 B2 * | 9/2020 | O'Connor | A61B 17/80 |
| 2003/0236555 A1 * | 12/2003 | Thornes | A61B 17/842 606/232 |
| 2011/0270306 A1 * | 11/2011 | Denham | A61B 17/06166 606/228 |
| 2013/0123810 A1 * | 5/2013 | Brown | A61B 17/0401 606/144 |

(Continued)

*Primary Examiner* — Jessica Weiss
(74) *Attorney, Agent, or Firm* — ArentFox Schiff LLP; Joseph M. Maraia

(57) ABSTRACT

Methods of ankle syndesmosis repair include drilling a bone hole through a fibula and at least partially into a tibia. A first anchor, which may be an all-textile anchor, is inserted into the bone hole in the tibia such that the first anchor does not project from a surface of the tibia. The first anchor is slidably attached to a suture that is coupled to a second anchor, which may be a knotless anchor. The second anchor is inserted into the bone hole in the fibula such that the second anchor does not project from a surface of the fibula. The suture is tensioned to reduce a distance between the first anchor and the second anchor, thereby stabilizing and reducing the fibula to the tibia.

16 Claims, 10 Drawing Sheets

(56) References Cited

U.S. PATENT DOCUMENTS

2014/0277128 A1* 9/2014 Moore ............... A61B 17/8875
606/232
2015/0127051 A1* 5/2015 Kaiser .................. A61F 2/0811
606/232
2016/0074030 A1* 3/2016 Dreyfuss ............ A61B 17/0401
606/232
2018/0280066 A1* 10/2018 O'Connor .......... A61B 17/1615
2023/0320721 A1* 10/2023 Bahoora ............ A61B 17/1659
606/232

* cited by examiner

METHODS FOR ANKLE SYNDESMOSIS REPAIR

CROSS-REFERENCE TO RELATED APPLICATIONS

This application claims priority to and benefit of U.S. Provisional Application No. 63/602,790 filed Nov. 27, 2023, entitled ANKLE SYNDESMOSIS WITH SUTURE ANCHORS, the contents of which are incorporated herein by reference in their entirety for all purposes.

FIELD

The present disclosure relates to the field of ankle surgery and, more particularly, to ankle syndesmosis repair techniques.

BACKGROUND

Ankle injuries are among the most common of the bone and joint injuries. One ankle injury that may occur is a syndesmotic injury. The syndesmosis is a slightly movable joint where the contiguous bony surfaces of the tibia and fibula are united by strong fibrous ligaments, including the anterior inferior tibiofibular ligament (AITFL), the posterior inferior tibiofibular ligament (PITFL), and the interosseous ligament (IOL). Together, these ligaments stabilize the relative positioning of the tibia and fibula. In severe cases, ankle injuries can lead to chronic tibia and fibula instability and degenerative arthritis. In some trauma cases, moreover, the fibular bone may be fractured and require additional stability.

During syndesmotic injury repair, surgeons will sometimes fix the fibula and tibia bones together with a syndesmotic screw. The screw inhibits normal movement of the bones and, thereby, the corresponding joint. When the natural articulation of the joint is healed, the screw may be removed. However, syndesmosis screws have significant problems. For example, fatigue failure of the screws is common, resulting in screw breakage and fragments of the screw being buried in bone. These fragments may be both painful to the patient and difficult for the surgeon to retrieve.

In other syndesmotic injury repairs, suspension fixation with fasteners (such as buttons) on opposing cortices of the tibia and fibula can be used to fix the fibula and tibia bones together. Suspension fixation has the advantage of providing the joint with some range of motion due to the lower elastic modulus of the suture material. However, there is currently no fastener device capable of managing shear stress at the cortices of fixation as well as a screw, particularly when additional stability is required for extreme dislocations. Furthermore, requiring fasteners to sit proud of the exterior bone surface can cause problems for abrasion of surrounding tissue, and patients may be able to feel the fastener beneath the skin. It is therefore desirable to provide a method of ankle syndesmosis repair whereby the fixation elements do not project from a surface of the bones and that also avoids the risks associated with bone screws.

SUMMARY

The disclosure describes a method of ankle syndesmosis repair that places a soft body anchor and a hard body anchor into the joint space such that there is no protruding anchor on the bone surface. The first step of the method creates bone holes though the fibula and into the cortical layer of the tibia.

Once both hole sizes have been drilled, the soft body anchor can be deployed within the tibial hole. The suture from the soft body anchor can then be threaded through the hard body anchor, which is inserted into the fibular hole. The suture is then tensioned until the desired stability between the tibia and fibula is met.

Embodiments of the method of ankle syndesmosis repair may include one or more of the following, in any suitable combination.

In embodiments, the method includes drilling a bone hole through a first bone and at least partially into a second bone adjacent the first bone. A first anchor is inserted into the bone hole in the second bone such that the first anchor does not project from a surface of the second bone. The first anchor is slidably attached to a flexible member. The flexible member is attached to a second anchor. The second anchor is inserted into the bone hole in the first bone such that the second anchor does not project from a surface of the first bone. The flexible member is tensioned to reduce a distance between the first anchor and the second anchor, thereby stabilizing and reducing the first bone relative to the second bone.

In further embodiments, drilling the bone hole through the first bone and at least partially into the second bone includes drilling the bone hole with a drill passed through a guide. In embodiments, inserting the first anchor into the bone hole in the second bone includes inserting the first anchor through the guide. In embodiments, the first anchor is secured to a distal end of a driver tool configured for insertion through the guide and into the bone hole. In embodiments, drilling the bone hole through the first bone and at least partially into the second bone includes drilling the bone hole having a first diameter in the first bone and a second diameter in the second bone. The first diameter is selected to be larger than the second diameter. In embodiments, inserting the first anchor into the bone hole in the second bone includes inserting the first anchor in the bone hole such that ends of the flexible member extend freely from the bone hole in the first bone. In embodiments, coupling the flexible member to the second anchor includes passing the flexible member through an eyelet of the second anchor. In embodiments, the second anchor is secured to an inserter tool configured for insertion into the bone hole. In embodiments, tensioning the flexible member includes rotating a tensioning knob on the inserter tool.

In additional embodiments, the method further includes, after tensioning the flexible member to reduce a distance between the first anchor and the second anchor, trimming an excess of the flexible member. In embodiments, the method further includes, after tensioning the flexible member to reduce a distance between the first anchor and the second anchor, attaching the flexible member to a third anchor in the second bone. In embodiments, the method further includes, after tensioning the flexible member to reduce a distance between the first anchor and the second anchor, attaching the flexible member to a brace. In embodiments, the method is performed through or underneath a fibular plate. In embodiments, the first anchor is an all-textile anchor. In embodiments, the flexible member is tensionable to change a body of the first anchor from a first configuration, whereby the body is elongate, to a second configuration, whereby the body is compressed axially and extended radially to form an interference fit with the bone hole. In embodiments, the second anchor is a knotless anchor. In embodiments, the flexible member is suture tape. In embodiments, the guide includes a spring configured to provide pressure between the first bone and the second bone.

A reading of the following detailed description and a review of the associated drawings will make apparent these and other features and advantages. Both the foregoing general description and the following detailed description are explanatory only and are not restrictive of aspects as claimed.

BRIEF DESCRIPTION OF THE DRAWINGS

The disclosure will be more fully understood by reference to the detailed description, in conjunction with the following figures, wherein.

DETAILED DESCRIPTION

Figure 1A:
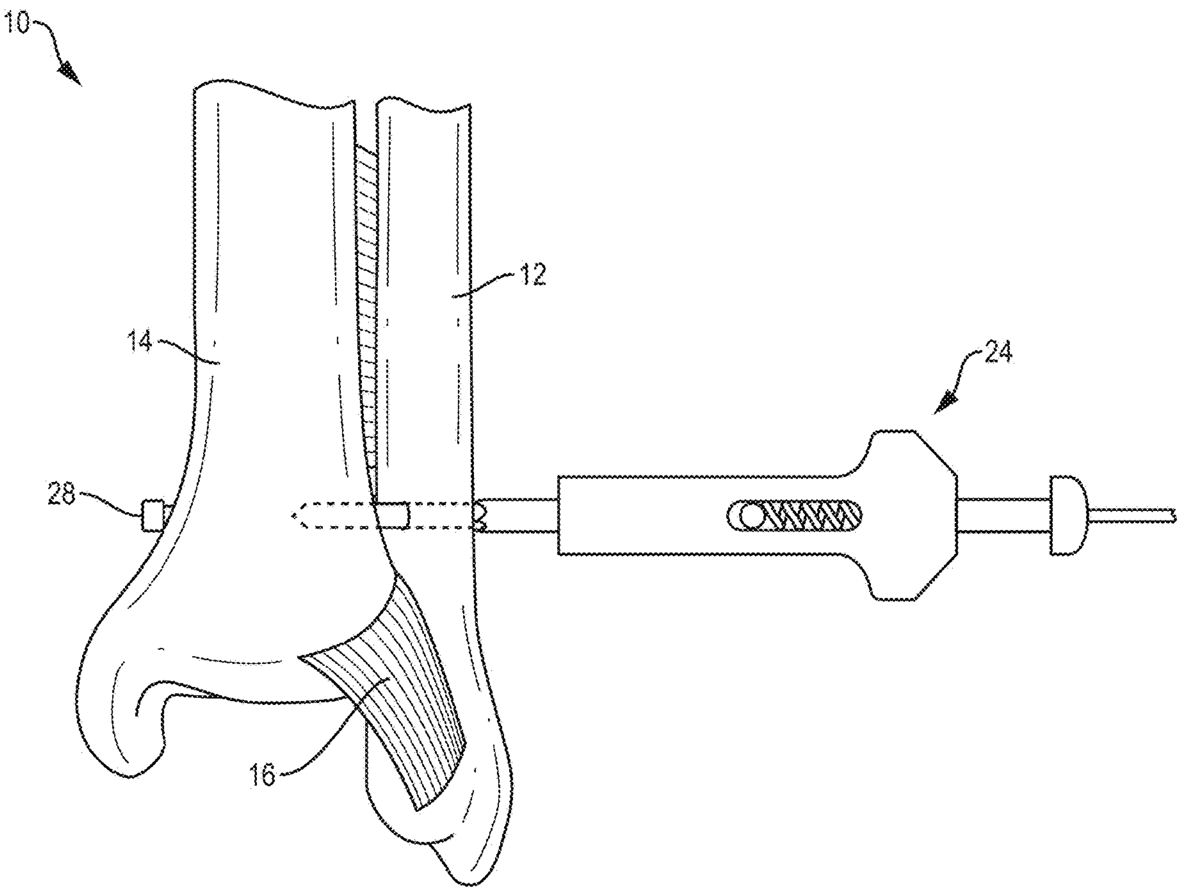
FIGS. 1A-1C illustrate an anterior view of an ankle joint including a first bone and a second bone, according to some embodiments of the disclosure.

In the description that follows, like components have been given the same reference numerals, regardless of whether they are shown in different embodiments. To illustrate embodiment(s) in a clear and concise manner, the drawings may not necessarily be to scale, and certain features may be shown in somewhat schematic form. Features that are described and/or illustrated with respect to one embodiment may be used in the same way or in a similar way in one or more other embodiments and/or in combination with or instead of the features of the other embodiments.

As used in the specification and claims, for the purposes of describing and defining the invention, the terms “about” and “substantially” are used to represent the inherent degree of uncertainty that may be attributed to any quantitative comparison, value, measurement, or other representation. The terms “about” and “substantially” are also used herein to represent the degree by which a quantitative representation may vary from a stated reference without resulting in a change in the basic function of the subject matter at issue. “Comprise,” “include,” and/or plural forms of each are open ended and include the listed parts and can include additional parts that are not listed. “And/or” is open-ended and includes one or more of the listed parts and combinations of the listed parts. Use of the relative terms “top,” “bottom,” “above,” “below” and the like helps only in the clear description of the disclosure and does not limit the structure, positioning and/or operation of the disclosure in any manner.

The following figures illustrate of a method of syndesmotic joint repair between the tibia and fibula of the ankle. However, the apparatus, systems, and methods described herein may also be used in other locations and/or procedures to provide approximation between two adjacent bones other than the tibia and fibula. %

Figures 1B, 1C:
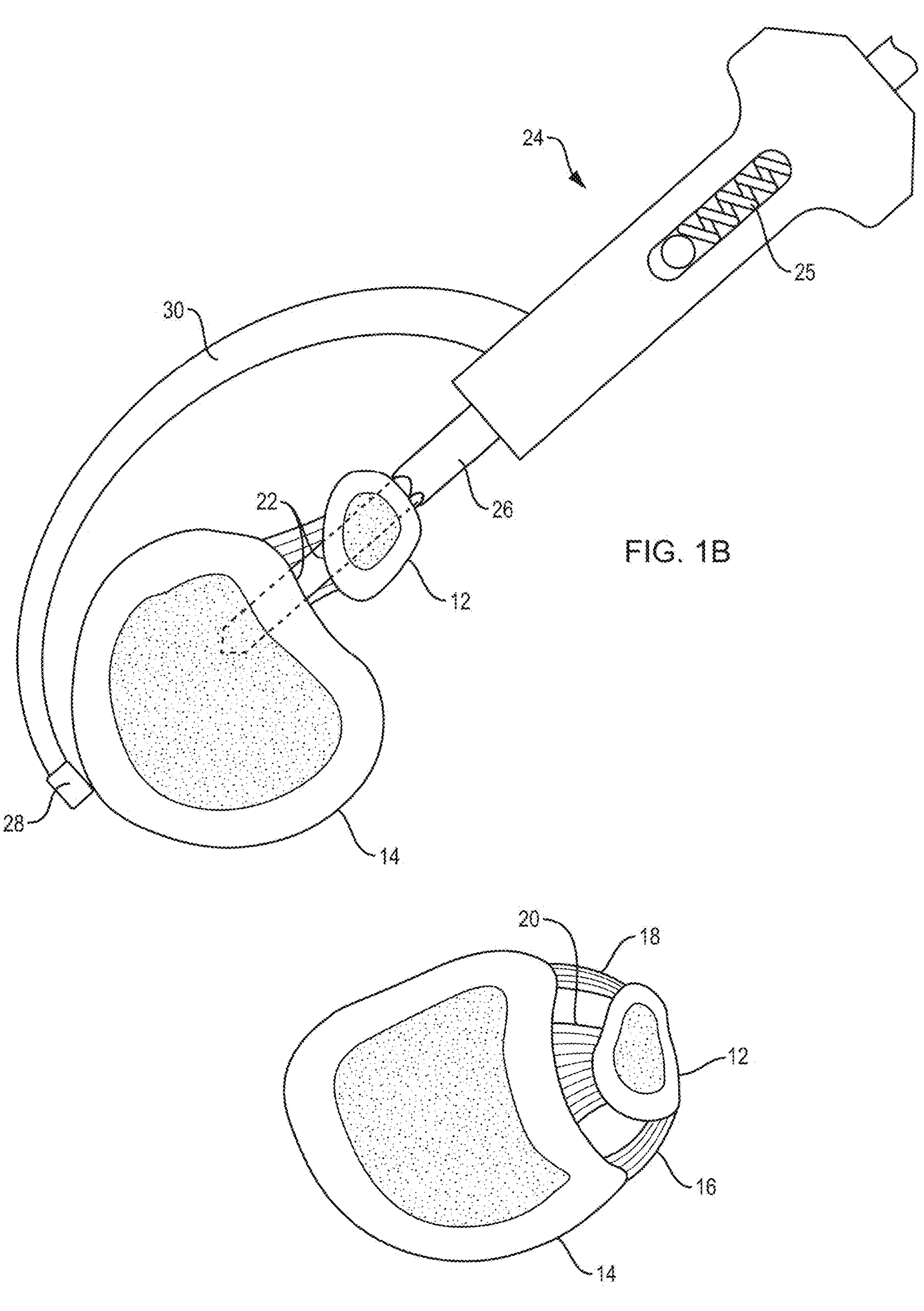

FIGS. 1A-1C illustrate anterior views of an ankle joint 10 including a first bone 12 (e.g., a fibula) and a second bone 14 (e.g., a tibia) according to some embodiments of the disclosure. FIG. 1A is a side view of the joint 10, while FIG. 1B is a top section view and FIG. 1C is a bottom section view. The AITFL 16, the PITFL 18, and the IOL 20 are also illustrated in FIGS. 1A-1C. Initially, a bone hole 22 may be drilled through the first bone 12 and at least partially into the second bone 14 at the appropriate location using conventional methods. For example, a user may provide a guide 24 to establish a drilling path for drill between a bullet 26 and a distal tip 28 of an arm 30 of the guide 24 to create the bone hole 22. In embodiments, the guide 24 may comprise a spring 25 configured to provide pressure in the appropriate trajectory between the first and second bones 12, 14. However, the disclosure contemplates other suitable configurations of the guide 24. In embodiments, the drill may use drill bits sized to create the bone hole 22 having a first diameter in the second bone 14 and a second diameter selected to the larger than the first diameter in the first bone 12. However, the disclosure contemplates that the bone holes 22 may have the same diameter in the first bone 12 and the second bone 14, or that the second diameter may be smaller than the first diameter.

Figure 2A:
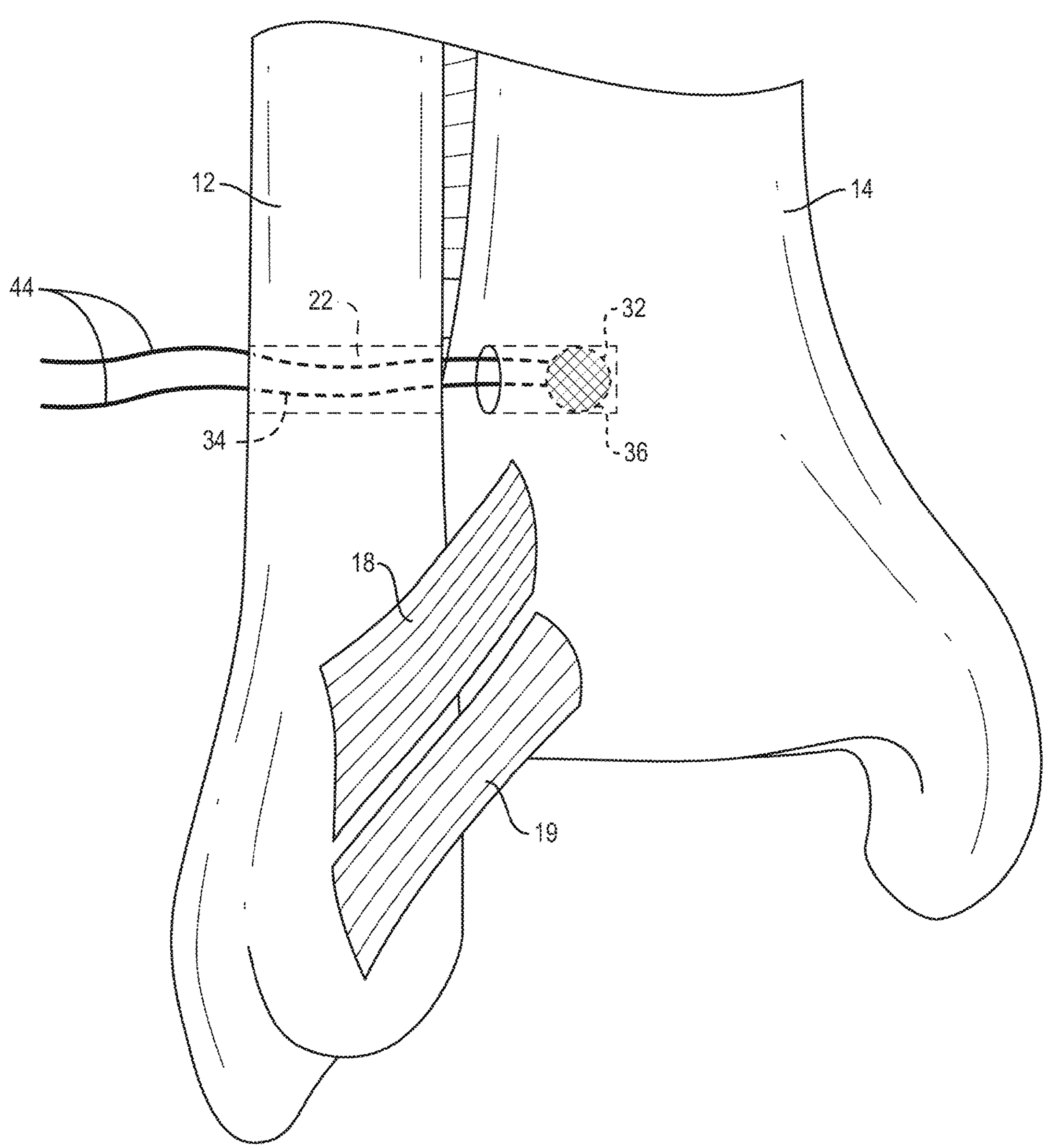
FIGS. 2A and 2B illustrate the placement of a first anchor within the bone hole in the second bone, according to some embodiments.
Figure 2B:
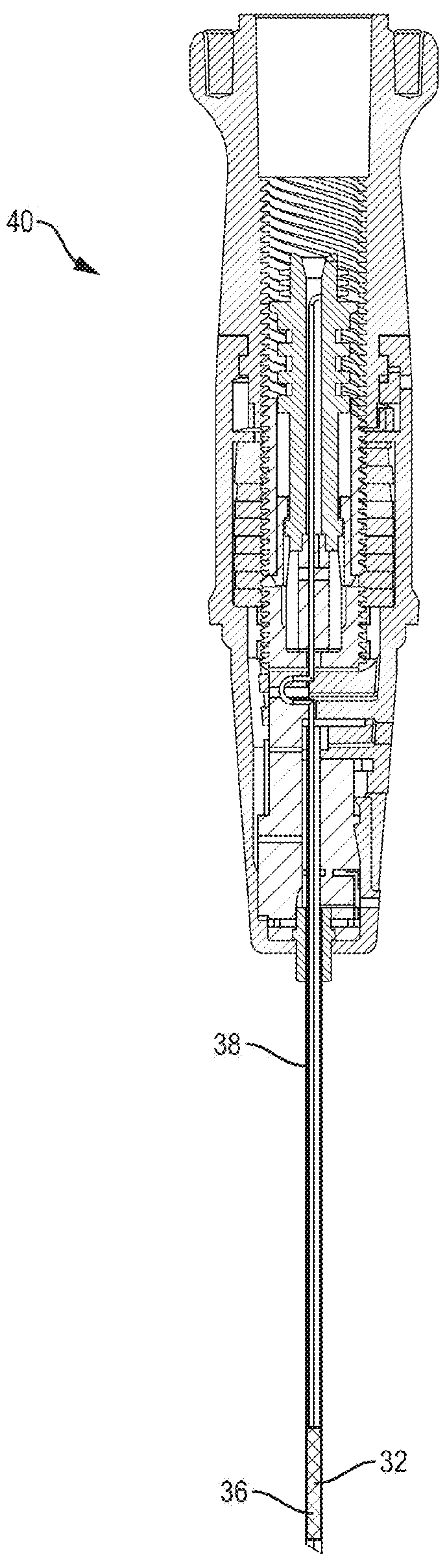

FIGS. 2A and 2B illustrate the placement of a first anchor 32 within the bone hole 22 in the second bone 14, according to some embodiments of the disclosure. In addition to the PITFL 18, the transverse ligament (TL) 19 is also illustrated in FIG. 2A. As shown in FIG. 2A, the first anchor 32 may be introduced through the guide 24 and threaded or pushed through the bone hole 22 into the second bone 14 to a desired depth. In some embodiments, the first anchor 32 may be an all-textile anchor, such as the anchor disclosed in U.S. Pat. No. 9,962,149 to Arthrocare Corporation (Austin, TX), incorporated herein by reference. In the first anchor 32, a flexible member 34 may be slidable with respect to a soft anchor body 36 and tensionable to change the anchor body 36 from a first configuration, in which the anchor body 36 is elongate, to a second configuration, in which the anchor body 36 is compressed axially and extended radially to form an interference fit with the bone hole 22. However, the disclosure contemplates other suitable anchors 32 where the flexible member 34 is slidable with respect to a body of the anchor, including barbed, threaded, screw-in, expanding, and interference fit anchors. Examples of the flexible member 34 can be made of suture tape. However, the disclosure contemplates that the flexible member 34 can be made from a variety of fibers or filaments including polymer, metallic or organic filaments, and can be made of resorbable and/or biologic materials. The flexible member 34 can include a coreless suture, or a suture with a jacket and a central core, and can be coated or uncoated. In some embodiments, the first anchor 32 may be coupled to the distal end 36 of the outer shaft 38 of a driver tool 40 (FIG. 2B) configured for insertion through the guide 24 and into the bone hole 22. Once the first anchor 32 is secured into the second bone 14 to the desired depth, the driver tool 40 and the guide 24 may be removed. As the driver tool 40 and guide 24 are removed, the proximal ends 44 of the flexible member 34 may slide through a lumen of the driver tool 40 and the bullet 26 of the guide 24 such that the proximal ends proximal ends 44 extend freely from the first bone 12.

Figure 3A:
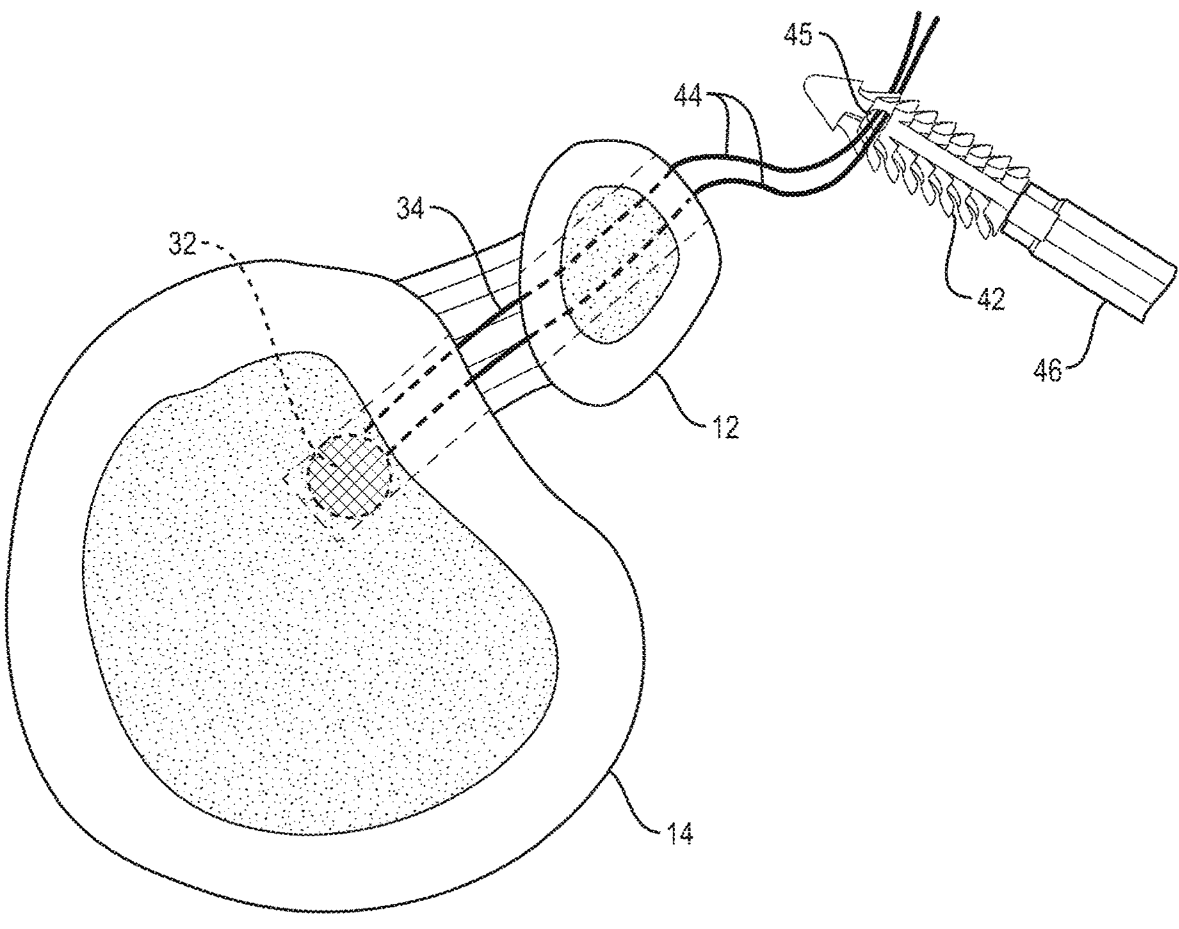
FIGS. 3A-3F illustrate the attachment of a flexible member to a second anchor, according to some embodiments.

FIGS. 3A-3E illustrate the attachment of the flexible member 34 to a second anchor 42, according to some embodiments of the disclosure. As shown in FIG. 3A, once the driver tool 40 has been removed, and proximal ends 44 of the flexible member 34 extend freely from the first bone 12, the proximal ends 44 can be coupled to the second anchor 42—for example, with a suture passer (not shown). The second anchor 42 may be engaged with an inserter tool 46 to rotate or otherwise advance the second anchor 42 into the first bone 12. In some embodiments, the second anchor 42 may be a knotless anchor configured to form an interference fit with the bone hole 22, such as the anchor disclosed in U.S. Pat. No. 9,936,939 to Smith & Nephew, Inc. (Memphis, TN), incorporated herein by reference.

Examples of the second anchor 42 can be manufactured from surgical stainless steel or other suitable biocompatible materials, such as titanium, nitinol, bio-absorbables, or non-absorbables (e.g., PEEK). The second anchor 42 can also comprise an all-textile anchor. In examples of the second anchor 42, the proximal ends 44 of the flexible member 34 may be passed through an eyelet 45 of the second anchor 42 and securable within the eyelet 45 by an internal body (not shown) without the need for tying knots in the flexible member 34.

Figure 3B:
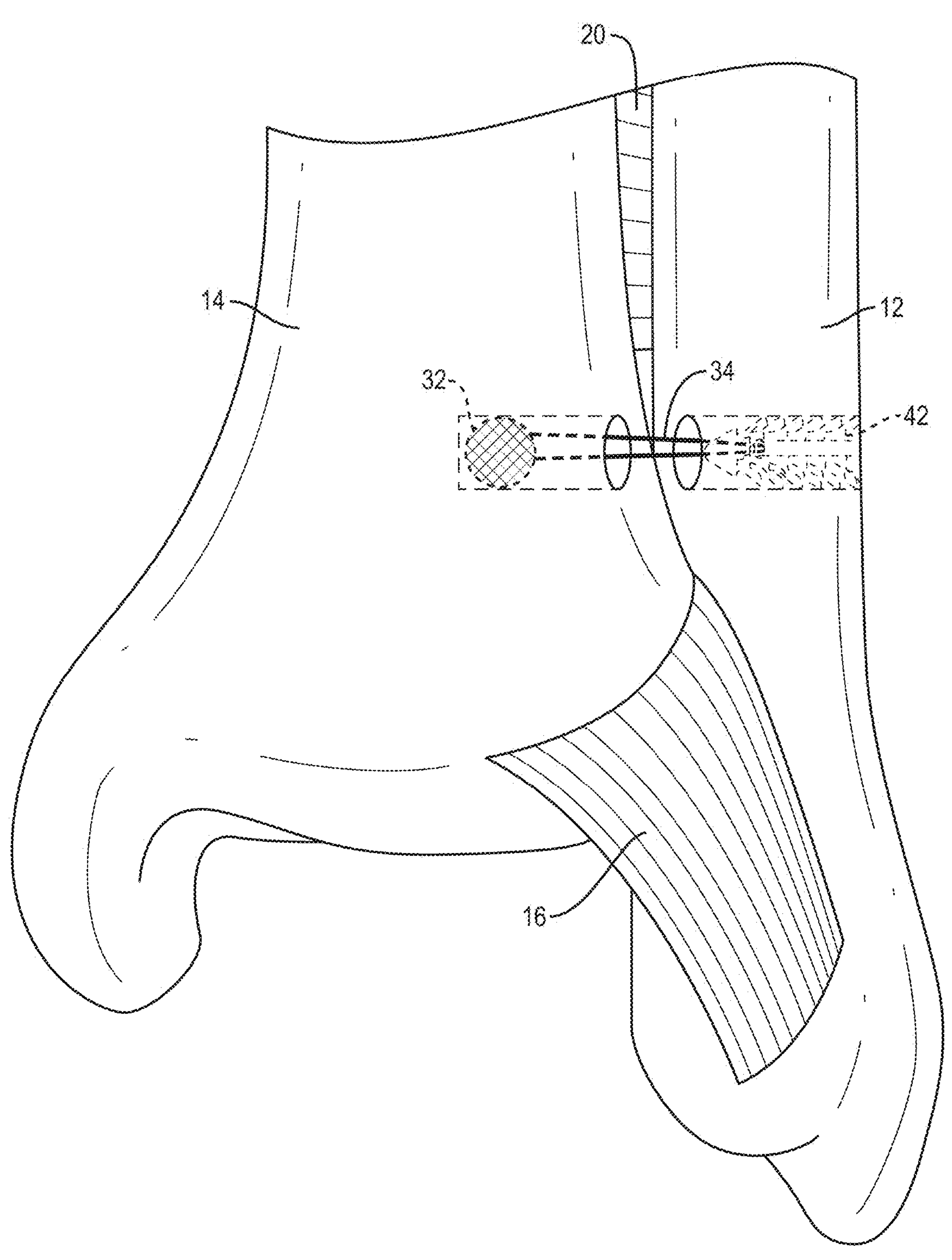
Figure 3C:
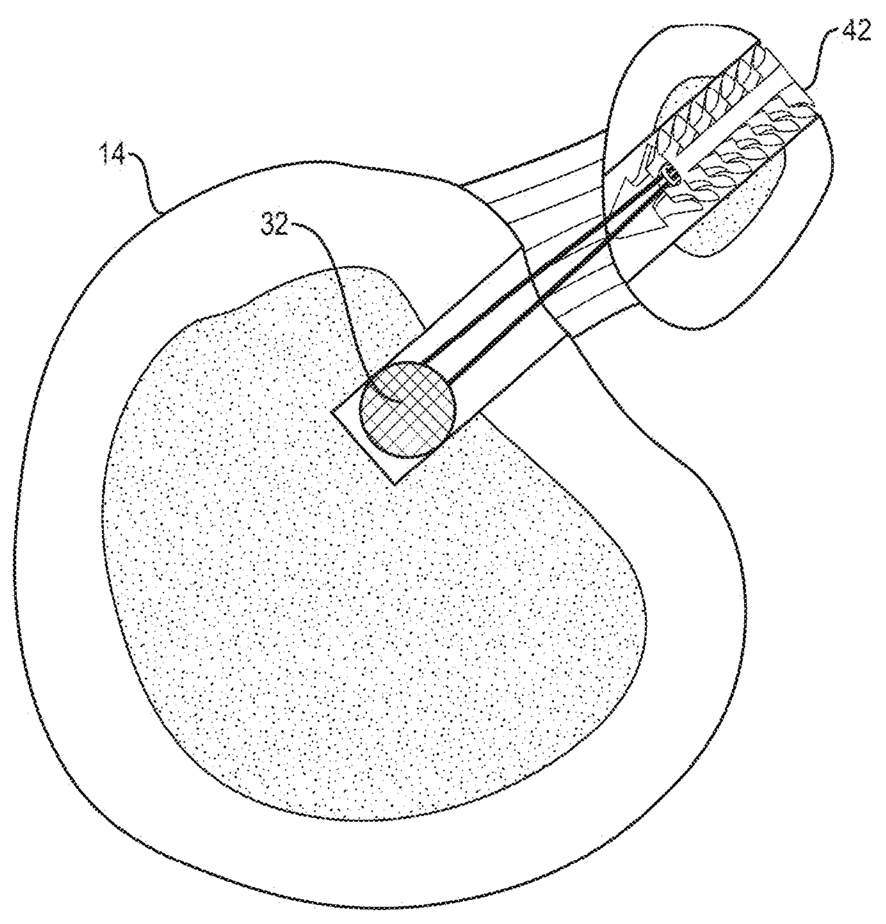
Figure 3D:
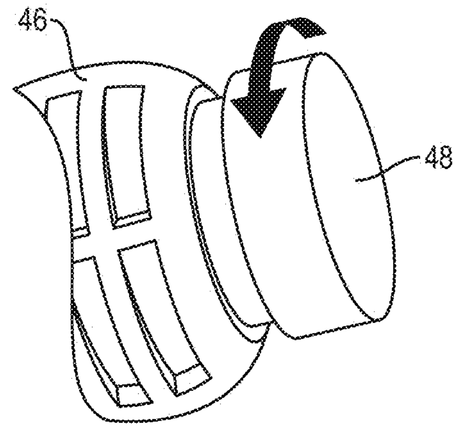
Figure 3E:
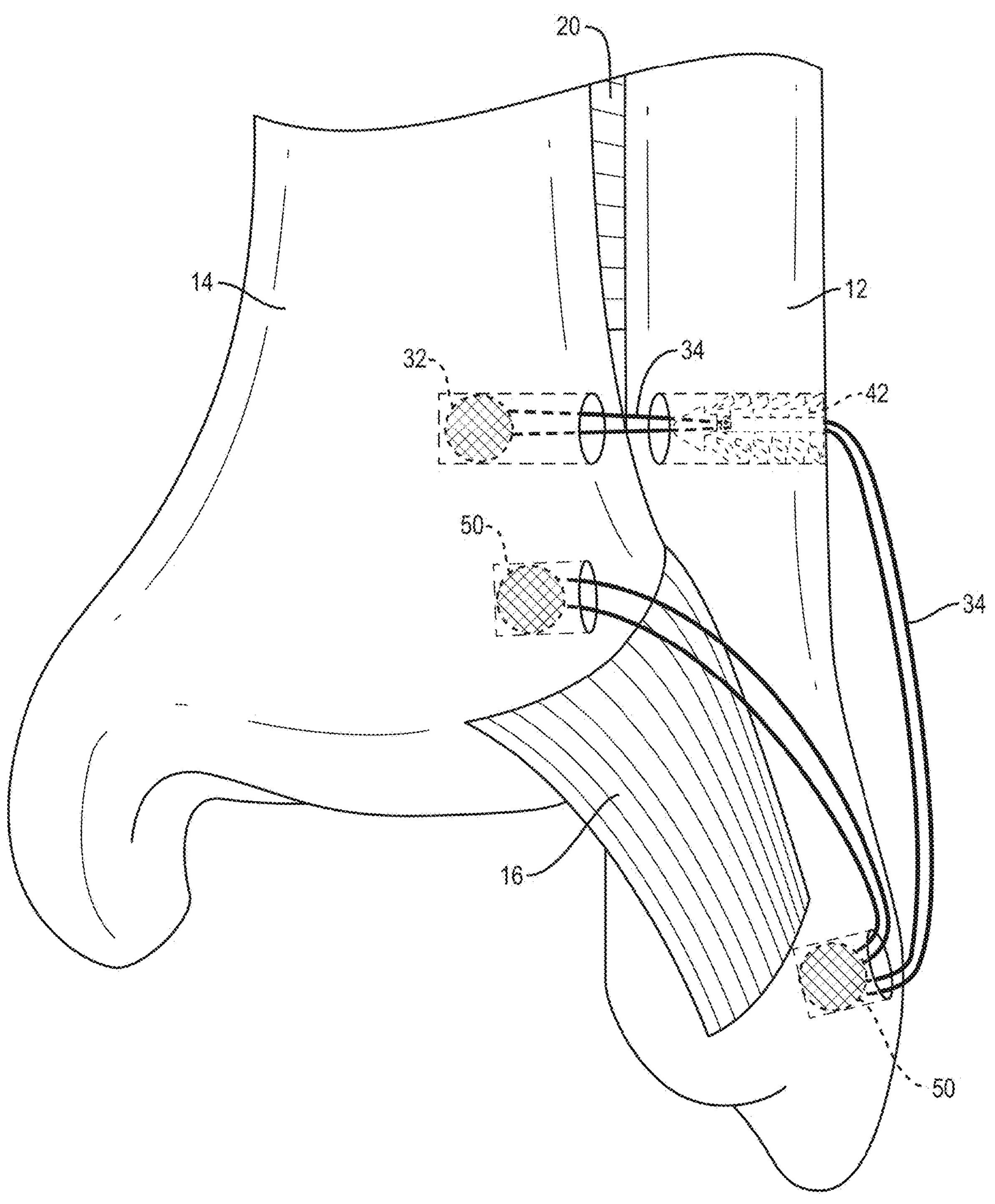
Figure 3F:
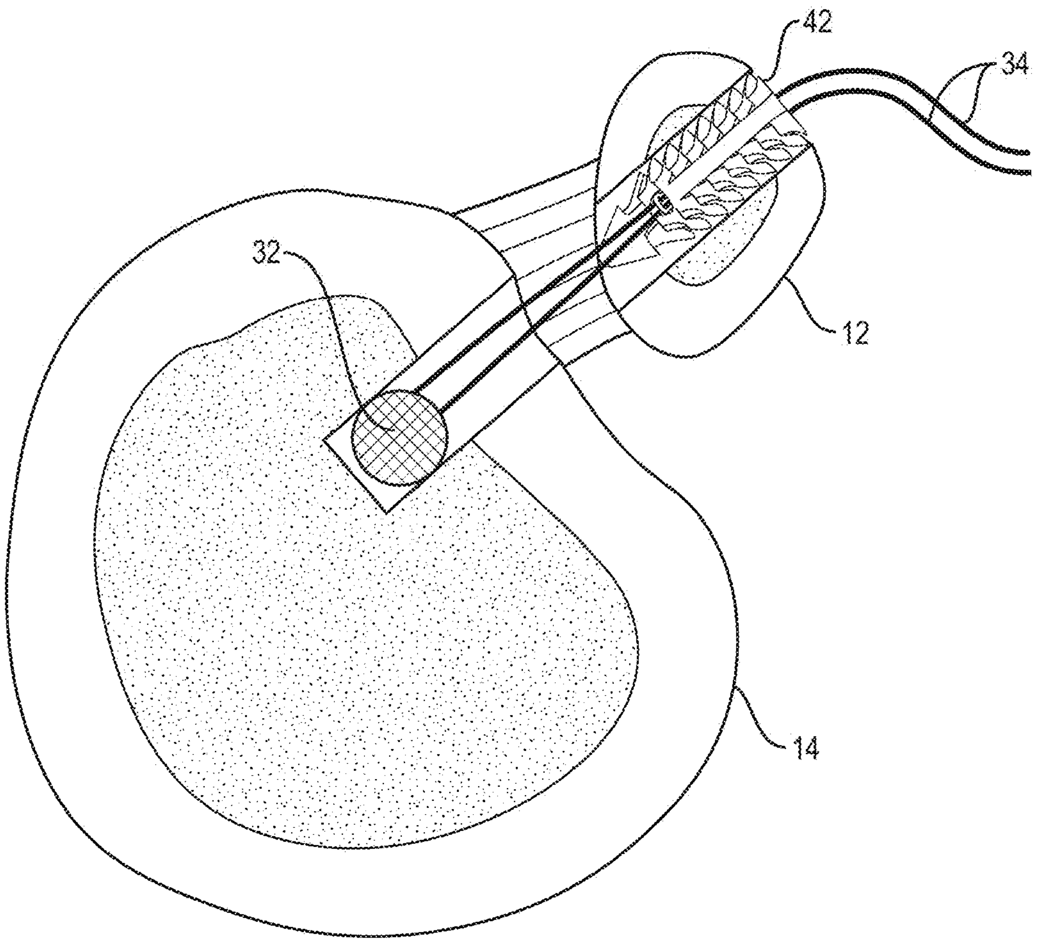

As shown in FIGS. 3B and 3C, once the flexible member 34 has been passed through the eyelet 45 of second anchor 42, the proximal ends 44 can be manipulated (e.g., tightened, loosened, etc.) to adjust the flexible member 34 to a desired length, thereby reducing the distance between the first and second bones 12, 14. For example, a tensioning knob 48 on the inserter tool 46 (FIG. 3D) may be rotated to tension the flexible member 34 until the desired stability between the first bone 12 and the second bone 14 is met. The flexible member 34 can then be secured to the anchor 42 and an excess of the flexible member 34 can be trimmed to complete the repair. Alternatively, the flexible member 34 may be secured to additional anchors 50 on the second bone 14 (FIG. 3E) that do not project from a surface of the second bone 14 or may extend from the first bone 12 to bracing needed for other ligaments (FIG. 3F).

Figure 4:
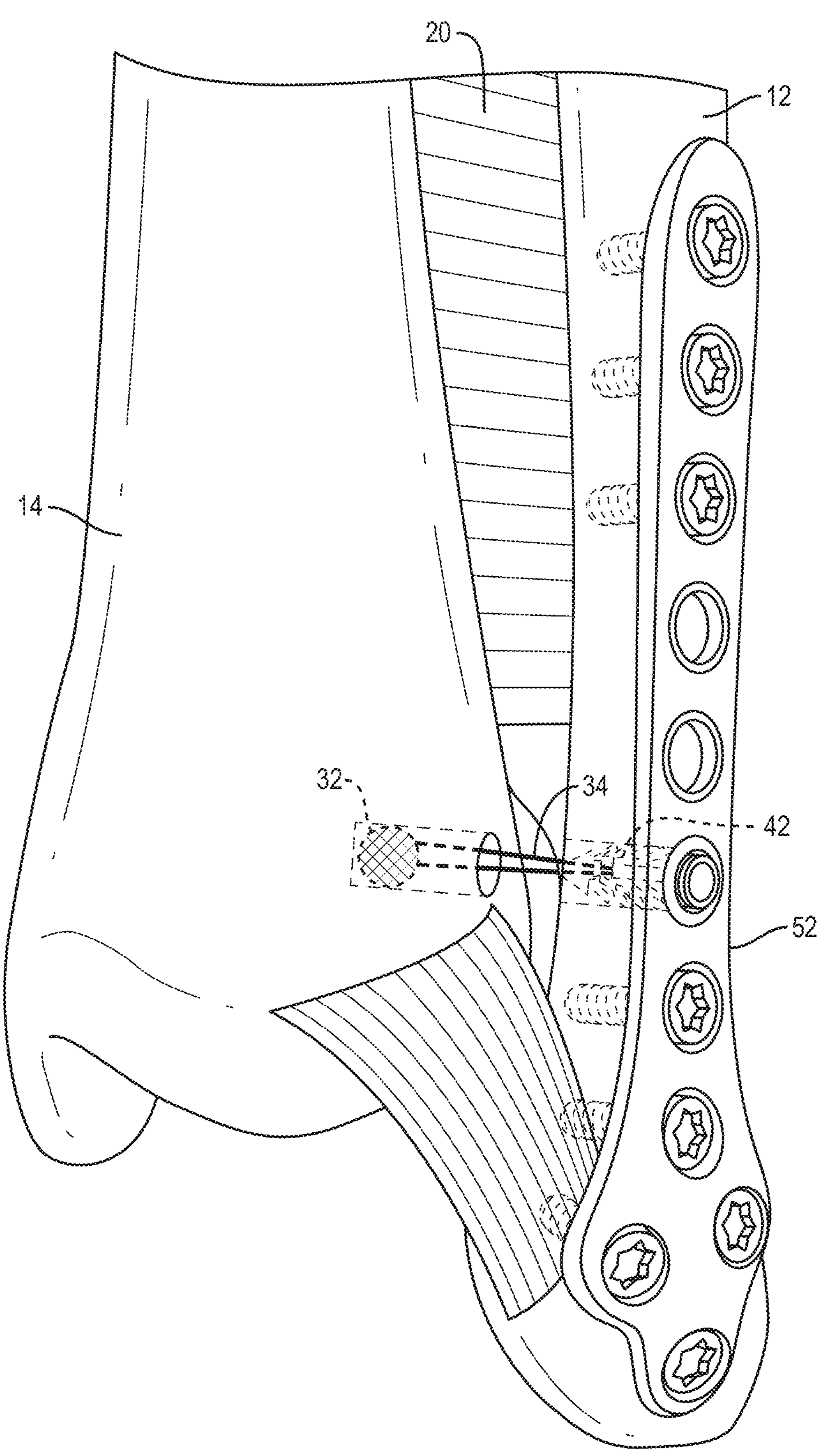
FIG. 4 illustrates a method of ankle syndesmosis repair using a fibular plate, according to some embodiments.

FIG. 4 illustrates an embodiment of a method of ankle syndesmosis repair using a fibular plate 52. As shown in FIG. 4, for trauma cases, the method described above with respect to FIGS. 1A-3F can also be performed either through a hole in the fibular plate 52 or underneath the fibular plate 52.

While the disclosure particularly shows and describes preferred embodiments, those skilled in the art will understand that various changes in form and details may exist without departing from the spirit and scope of the present application as defined by the appended claims. The scope of this present application intends to cover such variations. As such, the foregoing description of embodiments of the present application does not intend to limit the full scope conveyed by the appended claims.

What is claimed is:

1. A method of joint repair comprising:

drilling a single, continuous bone hole in a forward direction through a first bone and at least partially into a second bone adjacent the first bone;

inserting a first anchor into the bone hole in the second bone such that the first anchor does not project from a surface of the second bone, the first anchor slidably attached to a flexible member having two proximal ends;

passing the two proximal ends of the flexible member through a same eyelet of a second anchor such that the two proximal ends are securable within the eyelet without tying a knot with the two proximal ends;

inserting the second anchor into the bone hole in the first bone such that the second anchor does not project from a surface of the first bone; and tensioning the flexible member to reduce a distance between the first anchor and the second anchor, thereby stabilizing and reducing the first bone relative to the second bone.

2. The method of claim 1, wherein drilling the bone hole through the first bone and at least partially into the second bone comprises drilling the bone hole with a drill passed through a guide.

3. The method of claim 2, wherein inserting the first anchor into the bone hole in the second bone comprising inserting the first anchor through the guide.

4. The method of claim 3, wherein the first anchor is secured to a distal end of a driver tool configured for insertion through the guide and into the bone hole.

5. The method of claim 2, wherein the guide comprises a spring configured to provide pressure between the first bone and the second bone.

6. The method of claim 1, wherein drilling the bone hole through the first bone and at least partially into the second bone comprises drilling the bone hole having a first diameter in the first bone and a second diameter in the second bone, the first diameter selected to be larger than the second diameter.

7. The method of claim 1, wherein inserting the first anchor into the bone hole in the second bone comprises inserting the first anchor in the bone hole such that ends of the flexible member extend freely from the bone hole in the first bone.

8. The method of claim 1, wherein the second anchor is secured to an inserter tool configured for insertion into the bone hole.

9. The method of claim 8, wherein tensioning the flexible member comprises rotating a tensioning knob on the inserter tool.

10. The method of claim 1, further comprising, after tensioning the flexible member to reduce a distance between the first anchor and the second anchor, trimming an excess of the flexible member.

11. The method of claim 1, further comprising, after tensioning the flexible member to reduce a distance between the first anchor and the second anchor, attaching the flexible member to a third anchor in the second bone.

12. The method of claim 1, further comprising, after tensioning the flexible member to reduce a distance between the first anchor and the second anchor, attaching the flexible member to a brace.

13. The method of claim 1, wherein the method is performed through or underneath a fibular plate.

14. The method of claim 1, wherein the first anchor is an all-textile anchor.

15. The method of claim 1, wherein the flexible member is tensionable to change a body of the first anchor from a first configuration, whereby the body is elongate, to a second configuration, whereby the body is compressed axially and extended radially to form an interference fit with the bone hole.

16. The method of claim 1, wherein the flexible member comprises suture tape.

* * * * *